(12) United States Patent
Yamada

(10) Patent No.: US 8,419,737 B2
(45) Date of Patent: *Apr. 16, 2013

(54) BONE GRAFTING MATERIAL CONDENSING INSTRUMENT AND METHOD OF USE

(76) Inventor: Jason M. Yamada, Rolling Hills Estates, CA (US)

(*) Notice: Subject to any disclaimer, the term of this patent is extended or adjusted under 35 U.S.C. 154(b) by 136 days.

This patent is subject to a terminal disclaimer.

(21) Appl. No.: 13/134,080

(22) Filed: May 27, 2011

(65) Prior Publication Data

US 2011/0230921 A1    Sep. 22, 2011

Related U.S. Application Data

(63) Continuation of application No. 12/803,407, filed on Jun. 25, 2010, now abandoned, which is a continuation of application No. 11/895,812, filed on Aug. 28, 2007, now abandoned.

(60) Provisional application No. 60/882,940, filed on Dec. 31, 2006.

(51) Int. Cl.
*A61B 17/58* (2006.01)
*A61C 3/00* (2006.01)

(52) U.S. Cl.
USPC ........................................ 606/86 R; 433/141

(58) Field of Classification Search ................. D24/133, D24/152–154; 433/7, 72–75, 140–141, 143–144, 433/164, 167, 173, 215; 473/313; 606/79, 606/84, 86 R, 92–93, 170, 190, 242
See application file for complete search history.

*Primary Examiner* — Kevin T Troung
*Assistant Examiner* — Larry E Waggle, Jr.
(74) *Attorney, Agent, or Firm* — Robert R. Meads

(57) ABSTRACT

In an internal sinus manipulation procedure for augmenting bone of a dental patient between a bony floor of the patient's sinus and a raised portion of the patient's sinus membrane, employing a bone graft material condensing instrument comprising a longitudinally extending handle and a laterally extending distal head having an upper surface bounded by vertically extending substantially flat sides and a flat horizontally extending lower surface and placed within the raised portion of the patient's sinus membrane to condense a previously placed bone graft forming material upon a turning thereof.

1 Claim, 1 Drawing Sheet

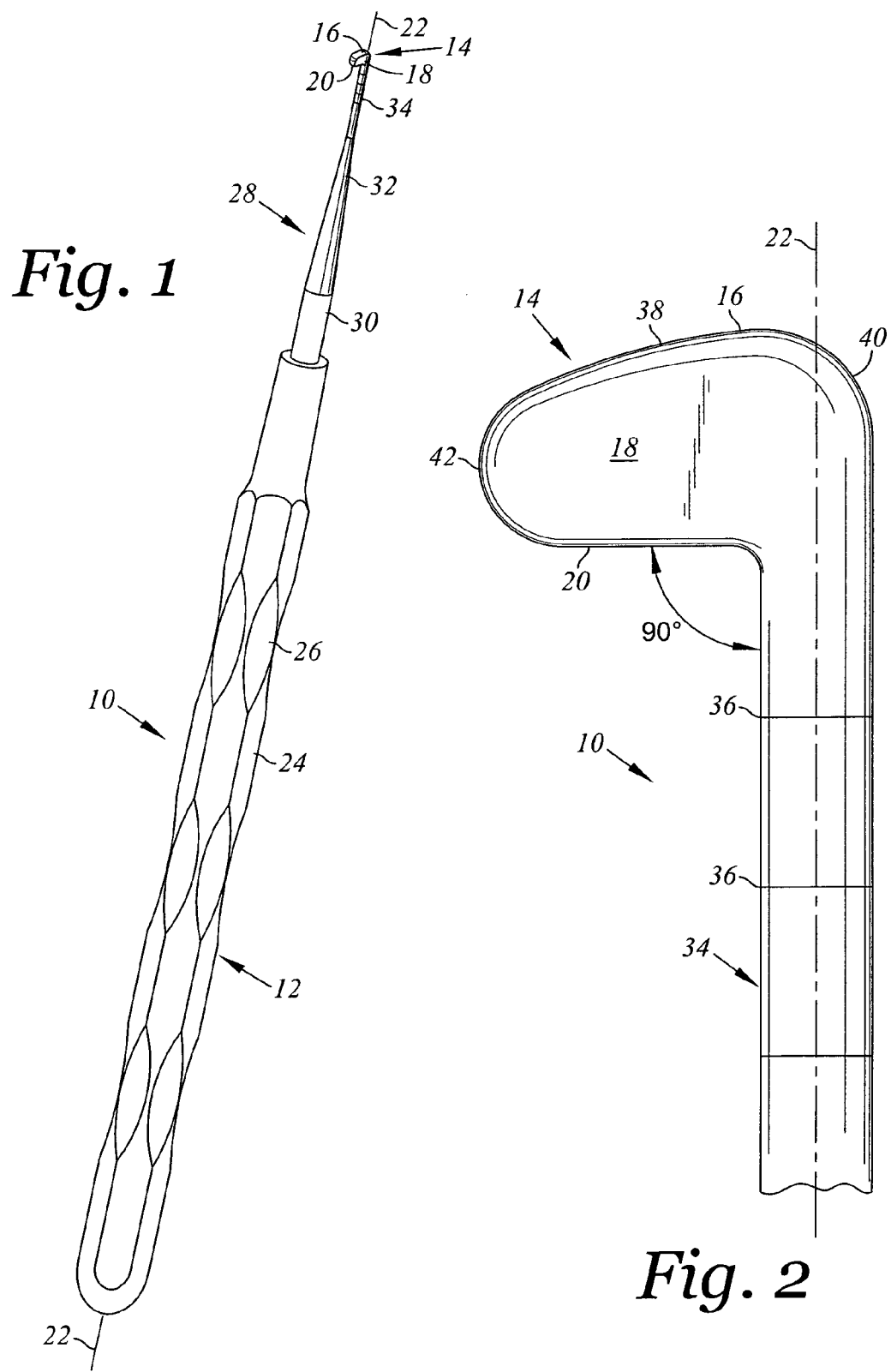

BONE GRAFTING MATERIAL CONDENSING INSTRUMENT AND METHOD OF USE

RELATED PATENT APPLICATIONS

The present application is a continuation and claims the benefits of U.S. patent application Ser. No. 12/803,407 filed Jun. 25, 2010 now abandoned, which is a continuation of Ser. No. 11/895,812 filed Aug. 28, 2007 now abandoned claiming the benefit of U.S. Provisional Patent application Ser. No. 60/882,940 filed Dec. 31, 2006. The present application also relates to and claims the benefits of the subject matter of U.S. patent application Ser. No. 11/895,823, also filed on Aug. 8, 2007, and entitled "Internal Sinus Manipulation (ISM) Procedure For Facilitating Sinus Floor Augmentation In Dental Procedures", now U.S. Pat. No. 7,662,188, issued Feb. 16, 2010 which is incorporated herein by this reference.

BACKGROUND OF INVENTION

As stated in the above-identified U.S. Pat. No. 7,662,188, during the described procedure, there is a pre-condensing and packing of a bone grafting material in a pocket between the sinus floor and the sinus membrane of a patient. This is accomplished using a bone condensing instrument. The present invention is directed to a preferred form of such a bone grafting material condensing instrument.

SUMMARY OF INVENTION

Basically, the bone grafting material condensing instrument of the present invention comprises a longitudinally extending handle carrying at its distal end a relatively small laterally extending bone graft material condensing head. The condensing head is designed to fit upward into a sinus bone channel containing a quantity of recently placed bone grafting material. The condensing head has an upper surface bounded by vertically extending substantially flat side surfaces and is employed to condense the bone graft packing material upon a simultaneous spinning of the handle on its longitudinal axis and a lateral movement of the instrument in the bone graft material.

BRIEF DESCRIPTION OF ACCOMPANYING DRAWINGS

FIG. 1 is a perspective view of a preferred bone graft material condensing instrument including a longitudinally extending handle and a relatively small laterally extending distal head having an upper surface, flat vertical sides and a flat lower surface extending horizontally relative to a longitudinal axis of the instrument.

FIG. 2 is an enlarged fragmentary sectional side view of an upper portion of the instrument of FIG. 1 showing the laterally extending distal head of the instrument.

DETAILED DESCRIPTION OF INVENTION

As depicted in FIG. 1, the bone graft material condensing instrument 10 of the present invention comprises a longitudinally extending handle 12 and a laterally extending distal head 14 having an upper surface 16 bounded by vertically extending substantially flat sides 18 and a flat horizontally extending lower surface 20.

As shown in FIG. 1, the handle 12 is longitudinally elongated on a longitudinal axis 22 of the instrument 10 and includes an enlarged lower hand-holdable portion 24 having a longitudinally fluted outer surface 26 for enhancing the gripability of the instrument 10.

As illustrated, the distal head 14 is secured to the handle by an intermediate longitudinally extending portion 28 of the instrument 10 comprising a cylindrical lower section 30, an axially elongated frusto-conical middle section 32 and an upper cylindrical section 34 of reduced diameter compared to the diameter of the lower section 30. As depicted in FIG. 1, the cylindrical lower section 30 is secured to and is of a slightly reduced diameter relative an upper end of the hand-holdable portion 24 of the handle 12. The bottom of the frusto-conical middle section 32 is secured to a top of the lower section 30, is axially elongated on the axis 22 and is reduced in lateral diameter as to approaches its relatively small upper end joined to a lower end of the upper cylindrical section 34. The upper cylindrical section 34, in turn, extends longitudinally on the axis 22 upward to support the distal head 14 that is secured to and supported by the end of the cylindrical section 34, as best shown in FIG. 2.

As shown in FIGS. 1 and 2, the outer surface of the upper cylindrical section 34 below the distal head 14 carries a plurality of horizontal vertically and evenly spaced depth markers 36 for indicating the user of the instrument 10 the depth of the instrument in a bone channel prior to use in the condensing of bone graft forming material. By way of example, the vertical spacing of the depth markers 36 may be about 2 millimeters.

As most clearly shown in FIG. 2, the distal head 14 extends upwardly from the upper end of the upper cylindrical section 34 and laterally from the longitudinal axis 22 of the instrument 10. An upper surface 38 of the distal head 14 extends from a downwardly curved rear portion 40 to a rounded forward end 42 of the head 14. Preferably as shown, the upper surface 38 is downwardly curved as it extends between the rear portion 40 and the forward end 42. Also, the head 14 preferably is about 2.5 millimeters from the forward-most edge of the section 34 to a forward-most point on the surface 42 as shown in FIG. 2. Also, from the a mid-point on the curve of the forward end 42 of the head 14 to the plane of the lower surface 20 is about 0.5 millimeters and from the lower surface 20 to a topmost portion of the upper surface 16 preferably is about 2 millimeters. In addition, the spacing of vertical sides 18 of the head 14 as they extend vertically between the upper surface 38 and the flat horizontally extending lower surface 20 preferably is about 1.5 millimeters and, as depicted in FIG. 2, the angle of the horizontally extending lower surface 20 to the vertically extending longitudinal axis 22 of the instrument 10 is preferably about 90 degrees.

As illustrated in FIG. 7 of the previously referenced U.S. Pat. No. 7,662,188, the instrument 10 preferably is designed in outward shape with the foregoing dimensions to efficiently pre-condense and pack the bone graft packing material in a pocket formed between the a sinus membrane and the floor of the sinus upon a spinning of the instrument on its longitudinal axis 22 while moving the instrument laterally and vertically in the pocket.

While a particular preferred embodiment of the instrument 10 has been illustrated and described above, it is appreciated that changes and modifications may be made in the illustrated embodiment without departing from the spirit of the invention. Accordingly, the scope of present invention is to be limited only by the terms of the following claim.

The invention claimed is:

1. In an internal sinus manipulation procedure for augmenting bone of a dental patient between a bony floor of the patient's sinus and a raised portion of the patient's sinus membrane, comprising:

creating an upward channel in bone within a maxillary posterior area of the patient such that an upper end of the channel extends to a base of the bony floor of the sinus and is sized to expose a portion of the patient's sinus membrane over the upper end of the upward channel;

lifting the exposed portion of the sinus membrane to form an open pocket between the sinus membrane and the bony floor;

introducing a bone grafting material through the upward channel into the open pocket; and compacting of the bone grafting material within the pocket, wherein the compacting of the bone grafting material comprises:

selecting a bone grafting material condensing instrument having a handle that extends upward and is elongated along a longitudinal axis of the instrument and a distal head extending upward from an upper end of the handle and including a downwardly curved rear portion, a rounded forward end, an upper surface extending between the downwardly curved rear portion and the rounded forward end, a flat horizontally extending lower surface extending between rounded forward end and the handle and vertically extending substantially flat sides bounding the upper and lower surfaces by extending vertically between the entire upper surface as it extends between the downwardly curved rear portion and the rounded forward end and the entire flat horizontally extending lower surface as it extends between the rounded forward end and the handle;

positioning the selected condensing instrument upwardly in the channel with the head of the instrument extending into the bone grafting material; and turning the handle of the selected condensing instrument on the longitudinal axis such that the head produces a mixing and lateral condensing of the bone grafting material within the pocket.

* * * * *